United States Patent
Maiorano et al.

(10) Patent No.: US 11,213,316 B2
(45) Date of Patent: Jan. 4, 2022

(54) GASKET WITH MULTI-LEAFLET VALVE FOR SURGICAL PORT APPARATUS

(71) Applicant: The Children's Medical Center Corporation, Boston, MA (US)

(72) Inventors: Anthony Maiorano, Waltham, MA (US); Jeffrey C. Cerier, Franklin, MA (US); Jake Ganem, Cape Neddick, ME (US)

(73) Assignee: The Children's Medical Center Corporation, Boston, MA (US)

( * ) Notice: Subject to any disclaimer, the term of this patent is extended or adjusted under 35 U.S.C. 154(b) by 593 days.

(21) Appl. No.: 15/917,126

(22) Filed: Mar. 9, 2018

(65) Prior Publication Data
US 2019/0274727 A1    Sep. 12, 2019

(51) Int. Cl.
*A61B 17/34* (2006.01)
*A61M 39/02* (2006.01)
*A61B 17/00* (2006.01)

(52) U.S. Cl.
CPC ..... *A61B 17/3423* (2013.01); *A61M 39/0247* (2013.01); *A61B 2017/00243* (2013.01); *A61M 2039/0279* (2013.01)

(58) Field of Classification Search
CPC ........ A61B 17/3423; A61B 2017/2948; A61B 17/3462; A61M 39/0247;
(Continued)

(56) References Cited

U.S. PATENT DOCUMENTS

| 2,243,992 A | 6/1941 | Wappler |
| 2,767,705 A | 10/1956 | Moore |

(Continued)

FOREIGN PATENT DOCUMENTS

| EP | 1426072 A1 | 6/2004 |
| EP | 2433551 A1 | 3/2012 |

(Continued)

OTHER PUBLICATIONS

European Patent Office, "Extended European Search Report", App. No. 17750861.1, dated Sep. 30, 2019, European Patent Office.
(Continued)

*Primary Examiner* — Brandy S Lee
*Assistant Examiner* — Nidah M Hussain
(74) *Attorney, Agent, or Firm* — Fish & Richardson P.C.

(57) ABSTRACT

A gasket for creating a fluid seal in a medical device includes a flexible base, a flexible hollow body, and a multi-leaflet valve. The flexible hollow body extends along an axis from a hole defined in the flexible base. The flexible hollow body is configured to have a relaxed state in which a cross section of the flexible hollow body has a first shape and a compressed state in which the cross section of the flexible hollow body has a second shape. The multi-leaflet valve is disposed in the flexible hollow body. The compressed state causes the multi-leaflet valve to close to increase (a) a first threshold force or a first threshold pressure differential needed to open the multi-leaflet valve in a distal direction and (b) a second threshold force or a second threshold pressure differential needed to open the multi-leaflet valve in a proximal direction.

27 Claims, 10 Drawing Sheets

(58) Field of Classification Search
CPC .. A61M 2039/0279; A61M 2039/0626; A61M 2039/064
USPC .......................................................... 604/167
See application file for complete search history.

(56) References Cited

U.S. PATENT DOCUMENTS

| | | |
|---|---|---|
| 4,180,068 A | 12/1979 | Jacobsen et al. |
| 4,201,199 A | 5/1980 | Smith |
| 4,233,982 A | 11/1980 | Bauer et al. |
| 4,436,087 A | 3/1984 | Ouchi |
| 4,535,773 A | 8/1985 | Yoon |
| 5,025,778 A | 6/1991 | Silverstein et al. |
| 5,217,001 A | 6/1993 | Nakao et al. |
| 5,256,149 A | 10/1993 | Banik et al. |
| 5,261,391 A | 11/1993 | Inoue |
| 5,279,551 A | 1/1994 | James |
| 5,352,206 A | 10/1994 | Cushieri et al. |
| 5,441,503 A | 8/1995 | Considine et al. |
| 5,454,791 A | 10/1995 | Tovey et al. |
| 5,454,807 A | 10/1995 | Lennox et al. |
| 5,458,633 A | 10/1995 | Bailey |
| 5,622,626 A | 4/1997 | Matkovich et al. |
| 5,632,782 A | 5/1997 | Carlough |
| 5,658,298 A | 8/1997 | Vincent et al. |
| 5,660,175 A | 8/1997 | Dayal |
| 5,752,970 A | 5/1998 | Yoon |
| 5,788,676 A | 8/1998 | Yoon |
| 5,797,960 A | 8/1998 | Stevens et al. |
| 5,842,971 A | 12/1998 | Yoon |
| 5,855,569 A | 1/1999 | Komi |
| 5,899,915 A | 5/1999 | Saadat |
| 5,928,218 A | 7/1999 | Gelbfish |
| 5,941,815 A | 8/1999 | Chang |
| 5,968,060 A | 10/1999 | Kellogg |
| 5,993,471 A | 11/1999 | Riza et al. |
| 6,017,333 A | 1/2000 | Bailey |
| 6,033,426 A | 3/2000 | Kaji |
| 6,129,713 A | 10/2000 | Mangosong et al. |
| 6,178,346 B1 | 1/2001 | Amundson et al. |
| 6,287,280 B1 | 9/2001 | Lampropoulos et al. |
| 6,293,282 B1 | 9/2001 | Lemelson |
| 6,309,345 B1 | 10/2001 | Stelzer et al. |
| 6,315,714 B1 | 11/2001 | Akiba |
| 6,379,326 B1 | 4/2002 | Cimino |
| 6,503,192 B1 | 1/2003 | Ouchi |
| 6,520,939 B2 | 2/2003 | Lafontaine |
| 6,554,793 B1 | 4/2003 | Pauker et al. |
| 6,641,562 B1 | 11/2003 | Peterson |
| 6,685,665 B2 | 2/2004 | Booth et al. |
| 6,689,085 B1 | 2/2004 | Rubenstein et al. |
| 6,749,559 B1 | 6/2004 | Kraas et al. |
| 7,442,167 B2 | 10/2008 | Dunki-Jacobs et al. |
| 7,537,562 B2 | 5/2009 | Takano |
| 7,914,444 B2 | 3/2011 | Moriyama et al. |
| 8,287,447 B2 | 10/2012 | Gasche et al. |
| 8,394,015 B2 | 3/2013 | DiBiasio et al. |
| 8,425,407 B2 | 4/2013 | Sato et al. |
| 8,491,631 B2 | 7/2013 | del Nido et al. |
| 8,926,502 B2 | 1/2015 | Levy et al. |
| 8,951,275 B2 | 2/2015 | Cannon et al. |
| 9,451,875 B2 | 9/2016 | Sigmon, Jr. et al. |
| 9,459,442 B2 | 10/2016 | Miller |
| 9,709,795 B2 | 7/2017 | Miller |
| 9,844,394 B2 | 12/2017 | DiBiasio et al. |
| 2002/0026094 A1 | 2/2002 | Roth |
| 2002/0068853 A1 | 6/2002 | Adler |
| 2002/0111585 A1 | 8/2002 | Lafontaine |
| 2002/0161378 A1 | 10/2002 | Downing |
| 2003/0009079 A1 | 1/2003 | Beaufore et al. |
| 2004/0024414 A1 | 2/2004 | Downing |
| 2004/0111019 A1 | 6/2004 | Long |
| 2004/0116897 A1 | 6/2004 | Aboul-Hosn |
| 2004/0191897 A1 | 9/2004 | Muschler |
| 2004/0193191 A1 | 9/2004 | Starksen et al. |
| 2005/0197530 A1 | 9/2005 | Wallace et al. |
| 2005/0234296 A1 | 10/2005 | Saadat et al. |
| 2005/0234298 A1 | 10/2005 | Kucklick et al. |
| 2006/0264708 A1 | 11/2006 | Horne, Jr. |
| 2007/0066869 A1 | 3/2007 | Hoffman |
| 2007/0197896 A1 | 8/2007 | Moll et al. |
| 2009/0048486 A1 | 2/2009 | Surti |
| 2009/0275893 A1 | 11/2009 | DiBiasio et al. |
| 2010/0286475 A1 | 11/2010 | Robertson |
| 2011/0245619 A1* | 10/2011 | Holcomb ........... A61B 17/3423 600/206 |
| 2011/0288372 A1 | 11/2011 | Petersen |
| 2011/0295072 A1* | 12/2011 | Boulais ................ A61B 5/064 600/176 |
| 2012/0209074 A1 | 8/2012 | Titus |
| 2012/0232342 A1 | 9/2012 | Reydel |
| 2013/0066281 A1* | 3/2013 | Yavorsky ............ A61M 5/162 604/257 |
| 2013/0245371 A1 | 9/2013 | Mourlas et al. |
| 2013/0281779 A1 | 10/2013 | Robertson |
| 2014/0213847 A1 | 7/2014 | Green et al. |
| 2014/0213848 A1 | 7/2014 | Moskowitz et al. |
| 2014/0221749 A1 | 8/2014 | Grant et al. |
| 2015/0065795 A1 | 3/2015 | Titus |
| 2015/0313633 A1 | 5/2015 | Gross et al. |
| 2016/0000463 A1 | 1/2016 | DiBiasio et al. |
| 2016/0367120 A1 | 12/2016 | Dupont et al. |
| 2017/0231477 A1 | 8/2017 | del Nido et al. |

FOREIGN PATENT DOCUMENTS

| | | |
|---|---|---|
| WO | 1998024501 A1 | 6/1998 |
| WO | 1998040016 A2 | 9/1998 |
| WO | 20040112652 A2 | 12/2004 |
| WO | 2005051175 A2 | 6/2005 |
| WO | 2007081800 A2 | 7/2007 |
| WO | 2011047339 A2 | 4/2011 |
| WO | 2016205694 A1 | 12/2016 |
| WO | 2017139629 A1 | 8/2017 |

OTHER PUBLICATIONS

Extended European Search Report issued in EP07716358.2 dated Apr. 24, 2014.
P. Dupont; "Invention Disclosure—Cardioscopes"; May 21, 2015; 5pp.
International Search Report & Written Opinion, PCT/US17/17445, dated May 5, 2017, 16 pages.
Extended European Search Report in European Application No. 16812547.4, dated Feb. 21, 2019, 8 pages.
International Search Report & Written Opinion, PCT/US07/00270, dated Oct. 1, 2007.
Ataollahi et al., "Cardioscopic Tool-Delivery Instrument for Beating-Heart Surgery," IEEE ASME Transactions on Mechatronics, 21(1):1-1 (abstract), Jan. 2015 [retrieved on Apr. 15, 2019]. Retrieved from the internet: <URL:https://www.researchgate.net/publication/283309805_Cardioscopic_Tool-Delivery_Instrumentfor_Beating-Heart_Surgery>.
International Search Report and Written Opinion in International Application No. PCT/US2016/038147, dated Sep. 8, 2016.
Vasilyev et al.; "A Novel Cardioport for Beating-Heart Image-Guided Intracardiac Surgery"; Children's Hospital Boston, Harvard Medical School, Boston, Massachusetts Institute of Technology, Cambridge, Massachusetts; International Society for Minimally Invasive Cardiothoracic Surgery (ISMICS); Jun. 3, 2009.
Vasilyev et al.; "Three-Dimensional Echo and Videocardioscopy-Guided Atrial Septal Defect Closure"; Annals of Thoracic Surgery; 2006; vol. 82; pp. 1322-1326.
Vasilyev et al.; "A novel cardioport for beating-heart, image-guided intracardiac surgery" The Journal of thoracic and Cardiovascular Surgery; vol. 142, No. 6; Dec. 2011; pp. 1545-1551.
Padala et al.; Transapical beating heart cardioscopy technique for off-pump visualization of heart valves; The Journal of thoracic and Cardiovascular Surgery; vol. 144, No. 1; 2012; pp. 231-234.

(56) References Cited

OTHER PUBLICATIONS

Shiose et al.; "Cardioscopy-guided surgery: Intracardiac mitral and tricuspid valve repair under direct visualization in the beating heart"; The Journal of thoracic and Cardiovascular Surgery; vol. 142, No. 1; 2011; pp. 199-202.
Uchida; "Recent Advances in Percutaneous Cardioscopy"; Curr Cardiovasc Imaging Rep; May 12, 2011; pp. 317-327.
Ahmed et al.; Initial clinical experience with a novel visualization and virtual electrode radiofrequency ablation catheter to treat atrial flutter; Heart Rhythm Society; 2011; pp. 361-367.
International Search Report and Written Opinion in International Application No. PCT/US17/17445, dated Jun. 6, 2017.
Ataollahi et al., "Cardioscopic Tool-Delivery Instrument for Beating-Heart Surgery," IEEE ASME Transactions on Mechatronics, vol. 21, No. 1, Feb. 2016, pp. 584-590.
ISA, "International Search Report", PCT/US2018/021797, dated May 23, 2018.

\* cited by examiner

GASKET WITH MULTI-LEAFLET VALVE FOR SURGICAL PORT APPARATUS

STATEMENT REGARDING FEDERALLY-SPONSORED RESEARCH

This invention was made with U.S. government support under Grant No. 5R42HL132655, awarded by the Heart, Lung, and Blood Institute (NHLBI) of the National Institutes of Health (NIH). The U.S. government has certain rights in the invention.

TECHNICAL FIELD

The present application relates generally to gaskets, fluid seals such as for use in surgical devices.

BACKGROUND

Instrument ports can be used to guide the insertion of surgical instruments into a surgical site. Examples of procedures where such instruments ports or guides are used are beating-heart, minimally-invasive cardiac procedures to repair heart defects or to treat vascular heart disease.

When an instrument port is inserted into a surgical site, it is exposed to bodily fluids such as blood, saliva, or urine. It is desirable to keep bodily fluids out of the instrument port to reduce the risk of contamination and infection to the patient and to prevent damage to electronics disposed in the instrument port.

There is a need for improved fluid seals for medical devices such as instrument ports.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

An aspect of the invention is directed to a gasket for creating a fluid seal in a medical device, the gasket comprising: a flexible base; a hole defined in the flexible base, the hole sized and arranged to align with a conduit in the medical device; a flexible hollow body extending along an axis from the hole, wherein the flexible hollow body is configured to have a relaxed state in which a cross section of the flexible hollow body has a first shape and a compressed state in which the cross section of the flexible hollow body has a second shape, the cross section lying in a plane orthogonal to the axis; and a multi-leaflet valve disposed in the flexible hollow body, wherein the compressed state causes the multi-leaflet valve to close to increase (a) a first threshold force or a first threshold pressure differential needed to open the multi-leaflet valve in a distal direction and (b) a second threshold force or a second threshold pressure differential needed to open the multi-leaflet valve in a proximal direction.

In one or more embodiments, the multi-leaflet valve is disposed at a distal end of the flexible hollow body and a proximal end of the flexible hollow body is disposed proximal to the hole in the flexible base. In one or more embodiments, the multi-leaflet valve is configured to open in response to an outward force from a surgical instrument inserted, in the distal direction, through the hole into a channel defined by the flexible hollow body, the outward force greater than or equal to the first threshold force required to open the multi-leaflet valve in the distal direction. In one or more embodiments, the multi-leaflet valve is configured to exert an inward force against the surgical instrument to close the multi-leaflet valve when the surgical instrument is removed therefrom. In one or more embodiments, the first threshold pressure differential required to open the multi-leaflet valve in the distal direction is lower than the second threshold pressure differential required to open the multi-leaflet valve in the proximal direction In one or more embodiments, an exposed surface of the multi-leaflet valve curves inwardly towards the flexible hollow body, the exposed surface facing away from the flexible hollow body. In one or more embodiments, the exposed surface is concave.

In one or more embodiments, the flexible hollow body is in the compressed state when the flexible hollow body is inserted into the conduit in the medical device. In one or more embodiments, a conduit radius of the conduit in the medical device is smaller than a largest cross-sectional radius of the flexible hollow body in the relaxed state. In one or more embodiments, the flexible hollow body exerts an outward force towards a wall of the conduit in the medical device to at least partially secure the flexible hollow body to the wall of the conduit.

In one or more embodiments, the gasket comprises silicone. In one or more embodiments, the first shape is irregular and the second shape is annular. In one or more embodiments, a second hole is defined in the flexible base, the second hole sized and arranged to align with a second conduit in the medical device.

Another aspect of the invention is directed to an instrument port for introducing an instrument into a surgical site, the instrument port comprising: a port body having a port body channel that extends from a proximal end to a distal end of the port body; a bulb comprising a bulb channel; and a gasket disposed between the port body and the bulb, the gasket comprising: a flexible base; a hole defined in the flexible base, the hole sized and arranged to align with the port body channel and the bulb channel to thereby form a continuous instrument channel; a flexible hollow body extending along an axis from the hole, wherein the flexible hollow body is configured to have a relaxed state in which a cross section of the flexible hollow body has a first shape and a compressed state in which the cross section of the flexible hollow body has a second shape, the cross section lying in a plane orthogonal to the axis; and a multi-leaflet valve disposed in the flexible hollow body, wherein the compressed state causes the multi-leaflet valve to close to increase (a) a first threshold force or a first threshold pressure differential needed to open the multi-leaflet valve in a distal direction and (b) a second threshold force or a second threshold pressure differential needed to open the multi-leaflet valve in a proximal direction.

In one or more embodiments, the flexible hollow body is in the compressed state when it is inserted into the bulb channel. In one or more embodiments, the flexible hollow body exerts an outward force towards a wall of the bulb channel to at least partially secure the flexible hollow body to the wall of the bulb channel. In one or more embodiments, the multi-leaflet valve is disposed at a distal end of the flexible hollow body and a proximal end of the flexible hollow body is disposed proximal to the hole in the flexible base.

In one or more embodiments, the multi-leaflet valve is configured to open in response to an outward force from a surgical instrument inserted through the instrument channel in the distal direction, the outward force greater than or equal to the first threshold force required to open the multi-leaflet valve in the distal direction. In one or more embodiments, the multi-leaflet valve is configured to exert an inward force against the surgical instrument to close the multi-leaflet valve when the surgical instrument is removed therefrom. In one or more embodiments, the first threshold pressure differential required to open the multi-leaflet valve in the distal direction is lower than the second threshold pressure differential required to open the multi-leaflet valve in the proximal direction.

In one or more embodiments, an exposed surface of the multi-leaflet valve curves inwardly towards the flexible hollow body, the exposed surface facing away from the flexible hollow body. In one or more embodiments, the exposed surface is concave. In one or more embodiments, a bulb channel radius of the bulb channel is smaller than a largest cross-sectional radius of the flexible hollow body in the relaxed state. In one or more embodiments, the gasket comprises silicone. In one or more embodiments, the first shape is irregular and the second shape is annular.

In one or more embodiments, a second hole is defined in the flexible base, the second hole sized and arranged to align with a second port body channel and a second bulb channel to thereby form a continuous imaging channel. In one or more embodiments, the second bulb channel extends to an imaging system disposed within the bulb.

BRIEF DESCRIPTION OF THE DRAWINGS

For a fuller understanding of the nature and advantages of the present concepts, reference is made to the following detailed description of preferred embodiments and in connection with the accompanying drawings, in which.

DETAILED DESCRIPTION

Figure 1:
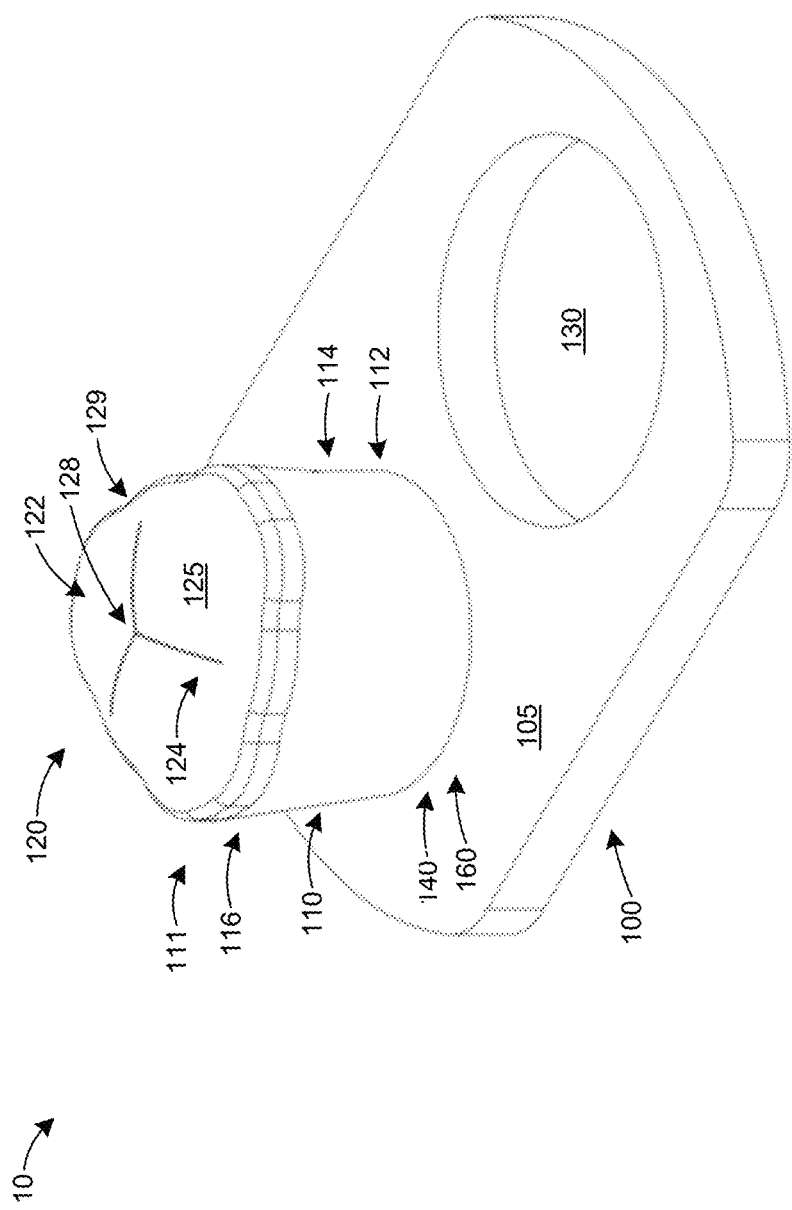
FIG. 1 is a perspective view of a gasket for creating a fluid seal in a medical device according to one or more embodiments.

A gasket for a medical device includes a flexible base, a flexible hollow body, and a multi-leaflet valve. The flexible hollow body extends from a hole defined in the flexible base. A flexible hollow body channel is defined in the flexible hollow body and aligned with the hole. The multi-leaflet valve is disposed at the distal end of the flexible hollow body. The multi-leaflet valve is configured to open in response to a force that is greater than or equal to a threshold force. However, the multi-leaflet valve is configured to remain closed in response to a force that is lower than a threshold force. The multi-leaflet valve is also configured to remain closed when the pressure differential across the multi-leaflet valve is lower than a threshold pressure differential, and it is configured to open when the pressure differential across the multi-leaflet valve is higher than a threshold pressure differential.

The second threshold pressure differential (sometimes referred to as the "cracking pressure") and second threshold force required to open the multi-leaflet valve in a proximal direction is significantly higher than the first threshold pressure differential and the first threshold force required to open the multi-leaflet valve in a distal direction, such that the multi-leaflet valve effectively operates as one-way valve in the distal direction to allow a surgical instrument to pass through in the distal direction. When the distal side of the gasket is exposed to bodily fluids (e.g., blood), the pressure on the distal side of the multi-leaflet valve is higher than the pressure on the proximal side of the multi-leaflet valve, which is exposed to air. The multi-leaflet valve is configured so that the pressure differential across the multi-leaflet valve due to its exposure to bodily fluids is significantly lower than the second threshold pressure differential (or cracking pressure) needed to open the multi-leaflet valve in a proximal direction.

In operation, the multi-leaflet valve opens in response to a force provided by an instrument that is inserted through the flexible hollow body channel in a distal direction, the force greater than or equal to the first threshold force. When the multi-leaflet valve is opened, it exerts an inward force against the instrument and closes when the instrument is removed. The multi-leaflet valve remains closed, and maintains a fluid seal, in response to a pressure differential across the multi-leaflet valve that is lower than the threshold pressure differential. For example, the multi-leaflet valve remains closed when a fluid, such as a liquid (e.g., saline), flows into the flexible hollow body channel and onto the proximal side of the multi-leaflet valve to clean the flexible hollow body channel before an instrument is inserted therethrough. The liquid can be removed by applying negative pressure (e.g., a vacuum) to one or more fluid return channels that is/are in fluid communication with the proximal end of the flexible hollow body channel.

The multi-leaflet valve also remains closed when it is exposed to fluids (e.g., bodily fluids) on the distal side of the multi-leaflet valve, for example when the gasket is inserted into a surgical site of a patient (e.g., when the gasket is disposed in a medical instrument such as an instrument port), as discussed above. The multi-leaflet valve is configured so that its cracking pressure (i.e., the second threshold pressure differential required to open the multi-leaflet valve in the proximal direction to allow bodily fluids to pass through in a proximal direction) or second threshold force, in a proximal direction, is significantly higher than the first threshold pressure differential or the first threshold force required to open the multi-leaflet valve in a distal direction (e.g., a force applied by an instrument when it is inserted through the multi-leaflet valve). As such, the multi-leaflet valve effectively operates as a one-way valve.

The flexible hollow body is configured to have a relaxed state and a compressed state. When the flexible hollow body is inserted (e.g., press fit) into a conduit (e.g., in a medical device such as an instrument port) that has a cross-sectional radius that is smaller than the largest cross-sectional radius of the flexible hollow body in the relaxed state, the flexible hollow body transitions to the compressed state. The flexible hollow body and optionally the flexible hollow body channel have a first shape (e.g., an irregular shape) in the relaxed state and a second shape (e.g., a second irregular shape, or a regular shape such as a circular or annular shape) in the compressed state. In the compressed state, the flexible hollow body exerts an outward force against the conduit wall to secure or partially secure the flexible hollow body to the conduit wall (e.g., to a portion of the medical device). The compressed state also causes the multi-leaflet valve to close, which increases the threshold force or threshold pressure differential (e.g., cracking pressure) needed to open the multi-leaflet valve in both directions (i.e., in the proximal and distal directions).

FIG. 1 is a perspective view of a gasket 10 for creating a fluid seal in a medical device according to one or more embodiments. The gasket 10 includes a flexible base 100, a flexible hollow body 110, and a multi-leaflet valve 120. In some embodiments, the gasket 10 (e.g., the flexible base 100, the flexible hollow body 110, and/or the multi-leaflet valve 120) comprises or consists of silicone (e.g., 70A durometer silicone). A first hole 140 and an optional second hole 130 are defined in the flexible base 100.

The second hole 130 is circular in FIG. 1 but it can be another shape (e.g., an oval, a square, a rectangle, etc.) in other embodiments. In some embodiments, the second hole 130 is arranged to align with a channel in a medical device, for example to pass wires or cables therethrough. In a specific example, the second hole 130 is arranged to align with an imaging channel in an instrument port, and electrical wires (e.g., for power, data, and/or controls) extend through the imaging channel, including the second hole 130, to a camera and/or a light source at the distal end (e.g., in an imaging bulb) of the instrument port. An example of such an instrument port is described in U.S. Pat. No. 8,394,015 and/or U.S. Patent Application Publication No. 2017/0231477, each of which is hereby incorporated by reference.

The flexible hollow body 110 extends from the first hole 140 defined in the flexible base 100. A proximal end 112 of the flexible hollow body 110 is disposed on the flexible base 100 such that a channel 150 (not illustrated in FIG. 1) in the flexible hollow body 110 is aligned with the first hole 140. FIG. 1 illustrates the flexible hollow body 110 in a relaxed state where the cross-sectional shape (e.g., a first shape 111) of the flexible hollow body 110 is irregular, where the cross section is parallel to a surface 105 of the flexible base 100. In the embodiment illustrated in FIG. 1, the surface 105 is planar.

The flexible hollow body 110 is configured to have a compressed state when the flexible hollow body 110 is inserted (e.g., press fit) into a channel of a medical device. In the compressed state, the cross-sectional shape of the flexible hollow body 110, in a plane parallel to the surface 105 of the flexible base 100, at least partially conforms to the cross-sectional shape of the channel. For example, when the flexible hollow body 110 is inserted into a tubular channel, one or more portions of the flexible hollow body 110 are compressed and/or deformed inwardly. The cross-sectional shape of the flexible hollow body 110 in the compressed state can be another irregular shape or it can be circular or annular to conform to the circular cross-sectional shape of the tubular channel. In another example, when the flexible hollow body 110 is inserted into a channel that has an oval cross-sectional shape, the cross-sectional shape of the flexible hollow body 110 in the compressed state can be an oval or an oval ring to conform to the cross-sectional shape of the channel. Inserting the flexible hollow body 110 into a channel of a medical device, such that the flexible hollow body 110 is in a compressed state, can cause a wall 114 of the flexible hollow body 110 to exert an outward force against the channel wall. The outward force of the wall 114 can cause the wall 114 and the channel wall to be in direct physical contact with each other to secure or partially secure the flexible hollow body 110 to the channel wall, thereby securing or partially securing the gasket 10 to the medical device.

The multi-leaflet valve 120 is disposed on a distal end 116 of the flexible hollow body 110. The multi-leaflet valve 120 includes 3 leaflets 122. A slit 124 separates each leaflet 122 from an adjacent leaflet 122. In other embodiments, the multi-leaflet valve 120 has more than 3 leaflets 122 (e.g., 4 leaflets to 10 leaflets) or only 2 leaflets 122. The exposed surface 125 of the multi-leaflet valve 120 curves towards the flexible hollow body 110 such that a center 128 of the multi-leaflet valve 120 is disposed further away from the flexible hollow body 110 than an edge 129 of the multi-leaflet valve 120. For example, the exposed surface 125 can be concave. In other embodiments, the exposed surface 125 can be planar or substantially planar. In yet other embodiments, the exposed surface 125 can be convex.

The multi-leaflet valve 120 is configured to open when at least a first minimum or a first threshold force is applied to the multi-leaflet valve 120 in a first direction, for example when a surgical instrument is inserted through the channel 150 in the flexible hollow body 110 from its proximal end 112 to its distal end 116. When a surgical instrument is inserted through the multi-leaflet valve 120, the force applied by the surgical instrument in the distal direction causes the leaflets 122 to open. The surgical instrument must be inserted with a force that is greater than the first minimum or the first threshold force required to open the leaflets 122 and multi-leaflet valve 120 in the distal direction. When the surgical instrument passes through the multi-leaflet valve 120, the leaflets 122 exert an inward force towards the surgical instrument so that they close when the surgical instrument is removed.

When the operating pressure differential across the multi-leaflet valve 120 is lower than a minimum pressure differential, the multi-leaflet valve 120 remains closed and a seal is maintained. The operating pressure differential is the difference between the pressure on the proximal and distal sides of the multi-leaflet valve. On the proximal side of the multi-leaflet valve 120, a first pressure can be applied when a fluid, such as saline, is introduced in the channel 150 in the flexible hollow body, for example to flush the channel 150 before a surgical instrument is inserted through the multi-leaflet valve 120. A negative pressure can also be applied to one or more fluid return channels that is/are in fluid communication with the proximal end of the channel 150 with a vacuum source. On the distal side of the multi-leaflet valve 120, a second pressure is applied when it is exposed to bodily fluids, such as when the gasket 10 is inserted into a surgical site in a patient as a component of an instrument port.

The multi-leaflet valve 120 is configured such that the minimum or threshold pressure differential (e.g., a second threshold pressure differential) needed to open the multi-leaflet valve 120 in a proximal direction (e.g., the cracking pressure), when the second pressure is higher than the first pressure, is significantly greater (e.g., an order of magnitude higher or between 2-10 times higher or any value or range therebetween) than the typical or maximum possible operating pressure differential across the multi-leaflet valve 120 when the multi-leaflet valve 120 is exposed to bodily fluids such as blood. The compression of the flexible hollow body 110 causes the channel wall to exert an inward force against the leaflets 122 of the multi-leaflet valve 120, which forces them closed and increases the minimum or threshold pressure differential needed to open the multi-leaflet valve 120 in a proximal direction to allow bodily fluids (e.g., blood) to flow in a proximal direction through the multi-leaflet valve 120.

The multi-leaflet valve 120 is further configured such that the minimum or threshold pressure differential (e.g., a first threshold pressure differential) needed to open the multi-leaflet valve 120 in a distal direction, when the first pressure is greater than the second pressure, is higher than the typical pressure differential across the multi-leaflet valve 120 when a fluid, such as saline, is introduced in the channel 150 in the flexible hollow body, such as to flush the channel 150 and the multi-leaflet valve 120.

Accordingly, the multi-leaflet valve 120 is configured so that its cracking pressure (i.e., the second threshold pressure differential required to open the multi-leaflet valve 120 in a proximal direction to allow bodily fluids to pass through the multi-leaflet valve 120 in the proximal direction) is significantly higher than the first threshold pressure differential required to open the multi-leaflet valve 120 in a distal direction. The multi-leaflet valve 120 is also configured so that the second minimum or the second threshold force required to open the multi-leaflet valve 120 in a proximal direction is significantly higher (e.g., an order of magnitude higher or between 2-10 times higher or any value or range therebetween) than the first minimum or the first threshold force required to open the multi-leaflet valve 120 in a distal direction (e.g., to allow a surgical instrument to pass through). As such, the multi-leaflet valve 120 effectively operates as a one-way valve.

Figure 2:
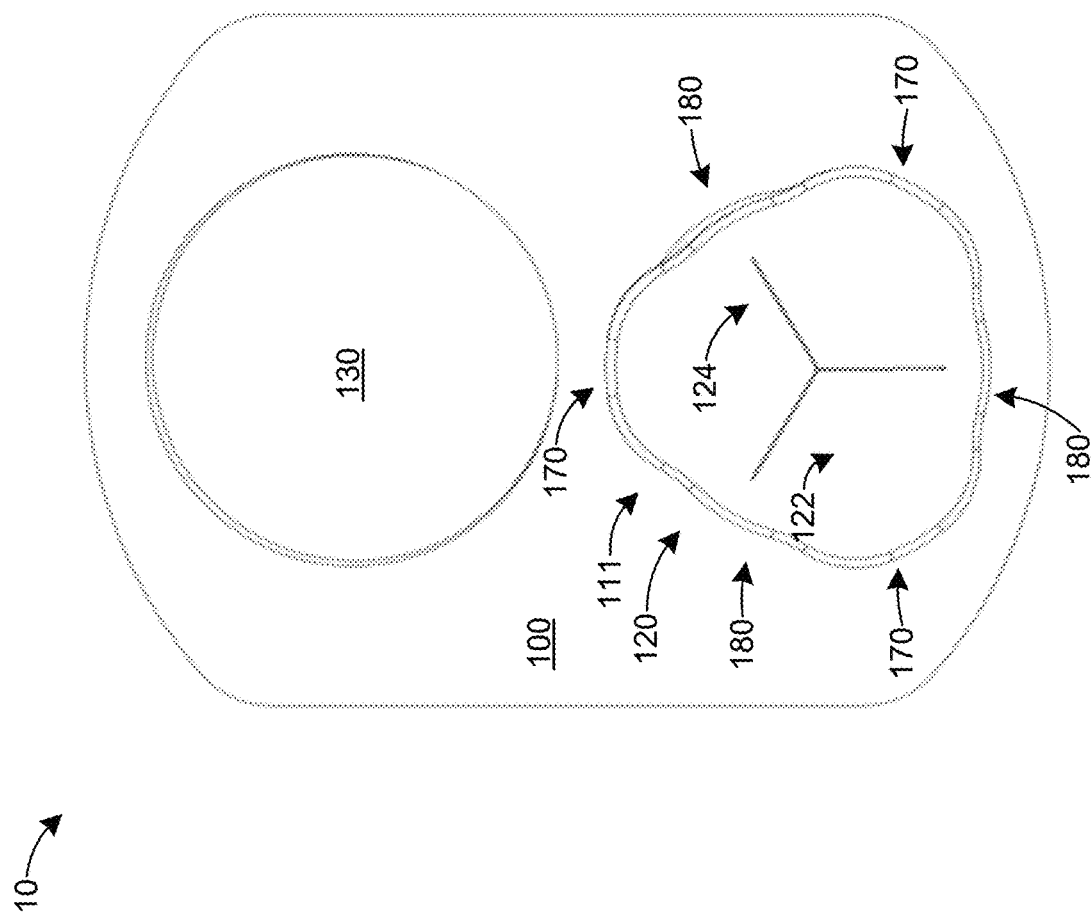
FIG. 2 is a top view of the gasket illustrated in FIG. 1.

FIG. 2 is a top view of the gasket 10 illustrated in FIG. 1 to further illustrate the irregular cross-sectional shape (e.g., first shape 111) of the flexible hollow body 110. As can be seen the cross-section shape of the flexible hollow body 110 is generally triangular with deformable contact points 170 at the "corners" of the triangle. Each leaflet 122 of the multi-leaflet valve 120 is aligned with a respective deformable contact point 170 such that an inward force applied to each deformable contact point 170 causes the respective leaflet 122 to close, thereby increasing the minimum pressure differential (e.g., the cracking pressure) needed to open the multi-leaflet valve 120. Each slit 124 of the multi-leaflet valve 120 is aligned with (i.e., orthogonal to) a respective side 180 of the triangle (i.e., the region between adjacent deformable contact points 170). In other embodiments, each slit 124 is aligned with a corresponding deformable contact point 170. In yet other embodiments, each slit is aligned at an angle (other than 90 degrees) with respect to a respective side 180 of the triangle.

As discussed above, the multi-leaflet valve 120 can have more than 3 leaflets 122 (e.g., 4 leaflets to 10 leaflets) or only 2 leaflets 122. Therefore, the multi-leaflet valve 120 can have only 2 or 3 or more (e.g., 4 to 10) deformable contact points 170 since each leaflet 122 is aligned with a corresponding deformable contact point 170.

Figure 3:
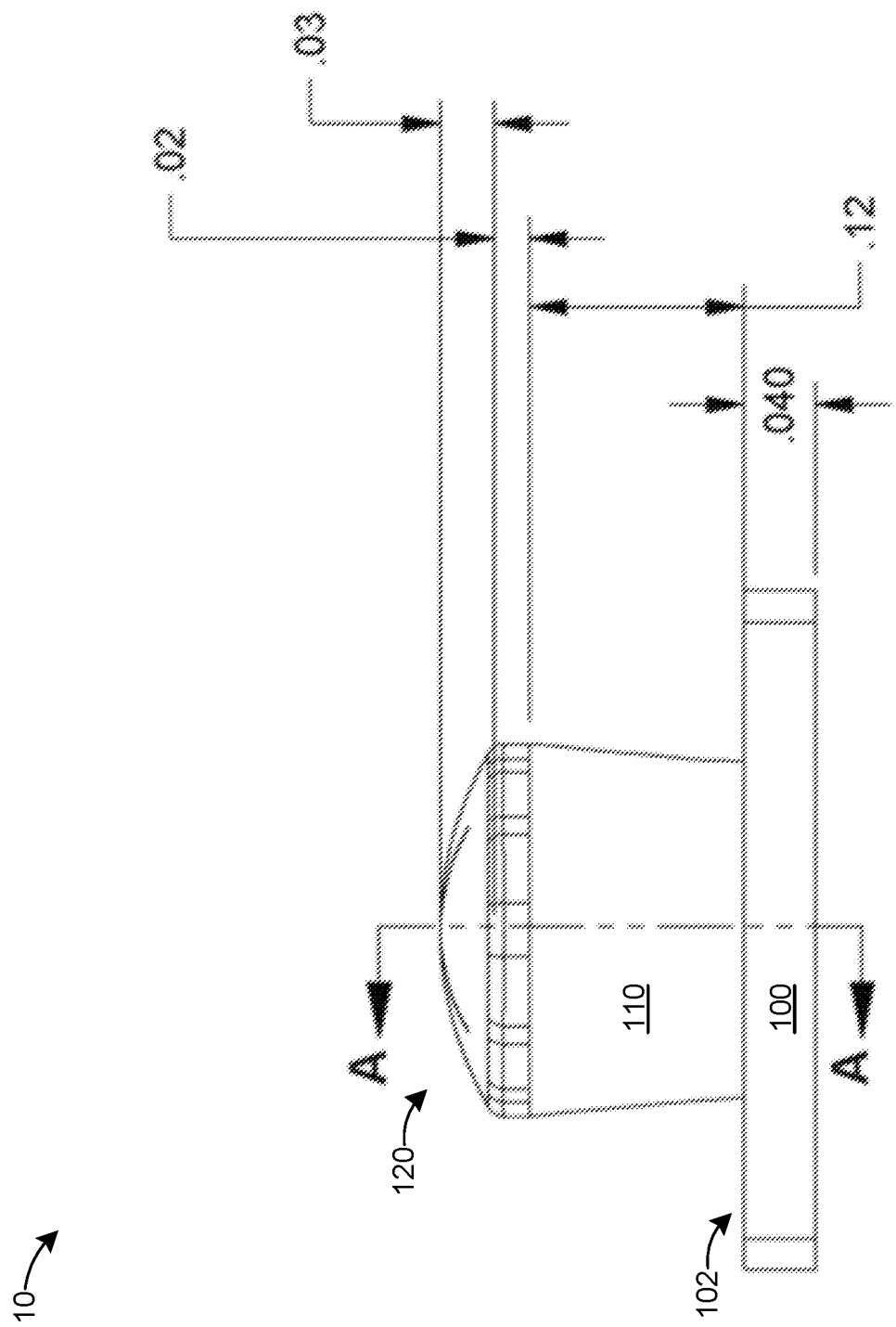
FIG. 3 is a side view of the gasket illustrated in FIGS. 1 and 2.

FIG. 3 is a side view of the gasket 10 illustrated in FIGS. 1 and 2 taken from an edge 102 of the flexible base 100. Representative dimensions (in inches) are illustrated in FIG. 3, but it is noted that these dimensions are exemplary and are not intended to be limiting.

Figure 4:
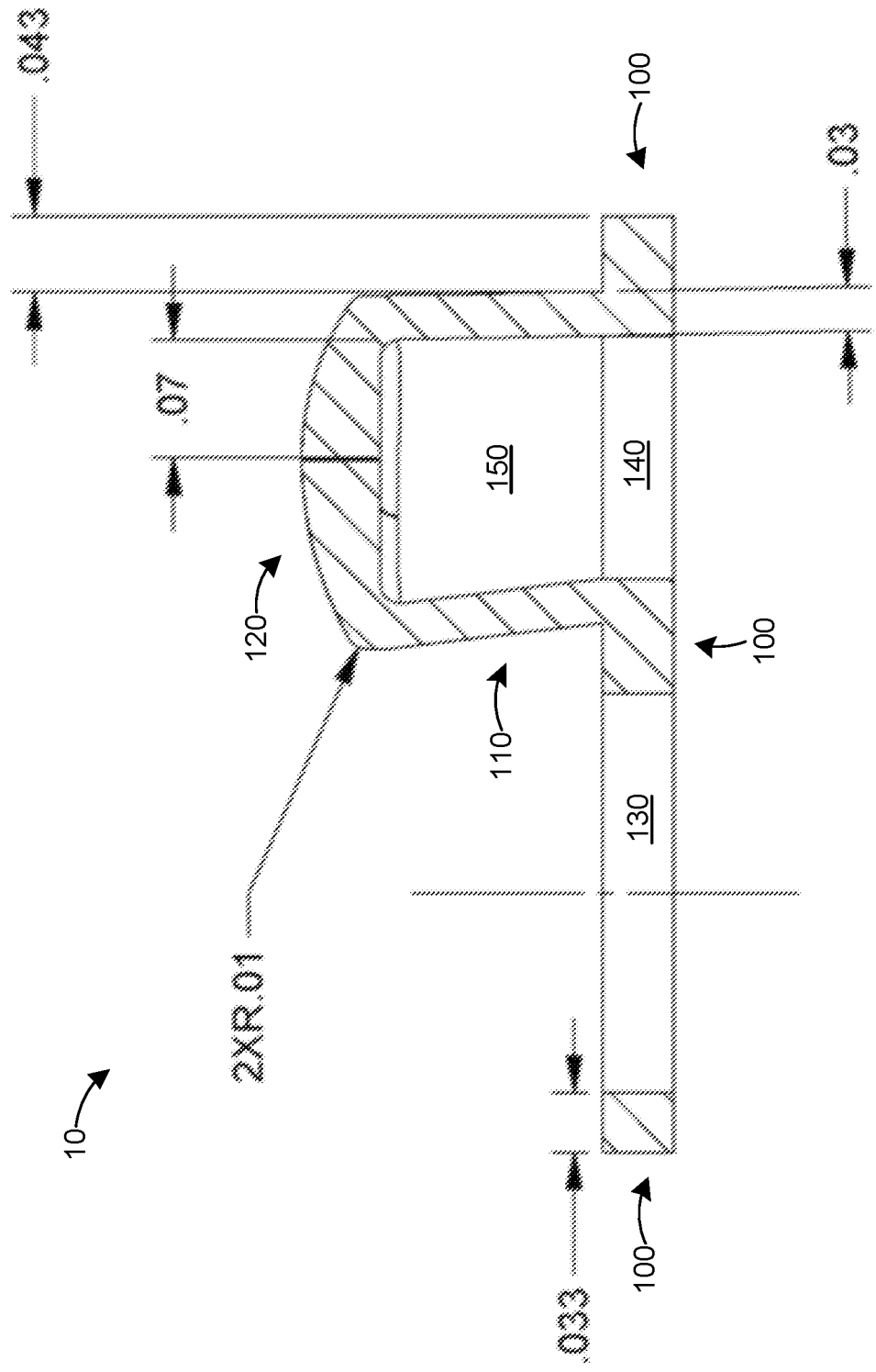
FIG. 4 is a cross-sectional view of the gasket illustrated in FIG. 3.

FIG. 4 is a cross-sectional view of the gasket 10 through line A-A in FIG. 3. The cross-sectional view in FIG. 4 reveals the channel 150 defined in the flexible hollow body 110. The channel 150 is aligned with and extends from the first hole 140. Representative dimensions (in inches) are illustrated in FIG. 4, but it is noted that these dimensions are exemplary and are not intended to be limiting.

Figure 5:
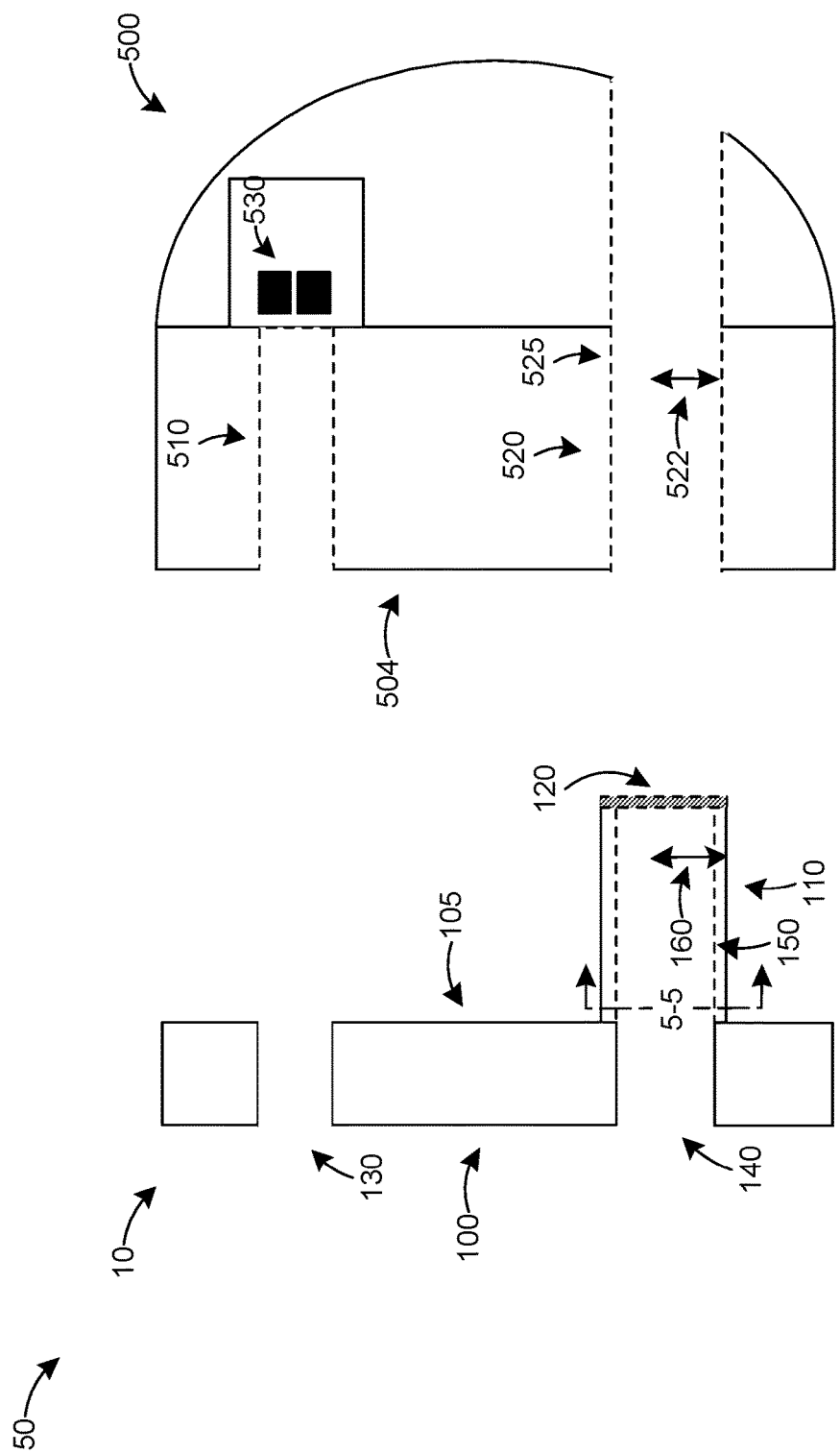
FIGS. 5 and 6 are side views of an assembly that includes a bulb that can be mechanically coupled to a gasket according to one or more embodiments.

FIG. 5 is a side view of an assembly 50 that includes a bulb 500 that can be mechanically coupled to the gasket 10, according to one or more embodiments. The bulb 500 includes first and second channels 510, 520. An imaging system 530 (e.g., a camera and an imaging source) is disposed within the bulb 500. The first channel 510 in the bulb 500 is aligned with the second hole 130 in the gasket 10. The second channel 520, defined by opposing walls 525, is configured to receive the flexible hollow body 110 including multi-leaflet valve 120. The cross-sectional radius 522 of the second channel 520 is smaller than the largest cross-sectional radius 160 of the flexible hollow body 110 in its relaxed state. In the arrangement illustrated in FIG. 5, the flexible hollow body 110 of gasket 10 is in the relaxed state.

Figure 6:
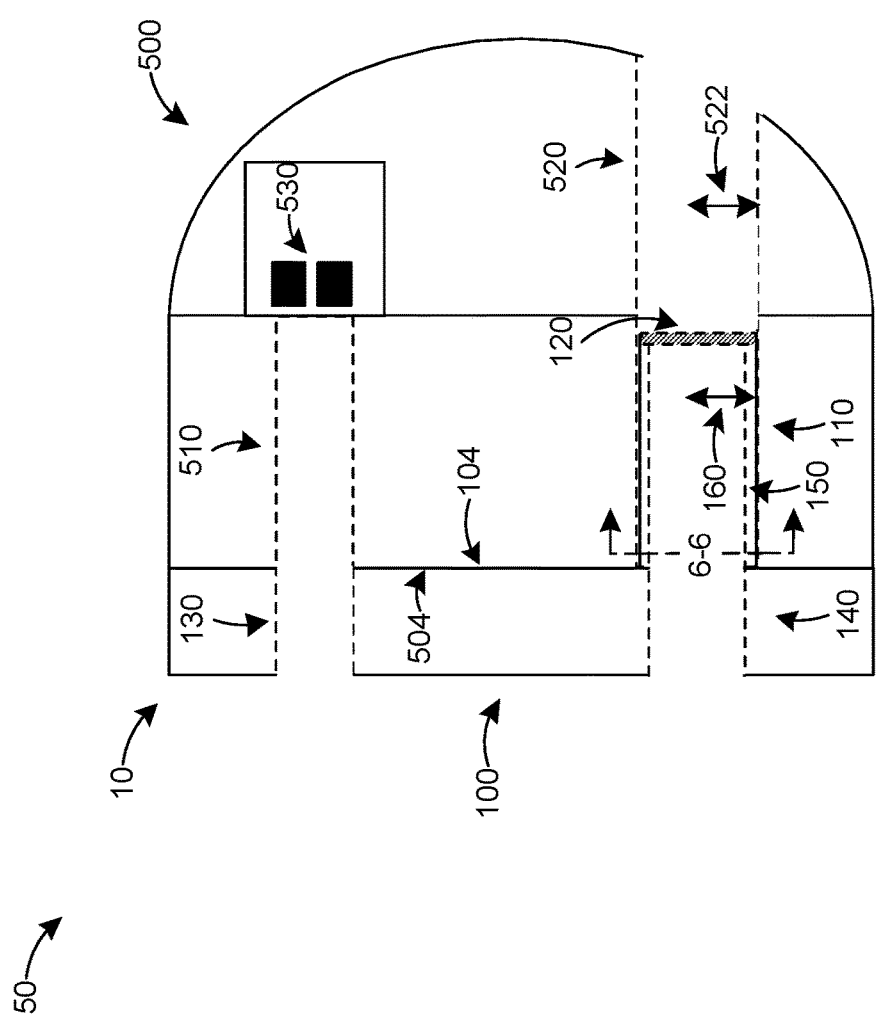

In operation, the gasket 10 is placed against (e.g., in direct physical contact with) the bulb 500, such that the surface 105 (e.g., the distal surface) of the base 100 is disposed against a proximal side 504 of the bulb 500, as illustrated in FIG. 6. In this position, the flexible hollow body 110 is inserted into the second channel 520 and the second hole 130 is disposed adjacent to and aligned with the first channel 510. Since the cross-sectional radius 522 of the second channel 520 is smaller than the largest cross-sectional radius 160 of the flexible hollow body 110 in its relaxed state, the flexible hollow body 110 is press fit into the second channel 520. The press-fitting causes the flexible hollow body 110 to transition from a relaxed state to a compressed state, as discussed herein.

Figure 7:
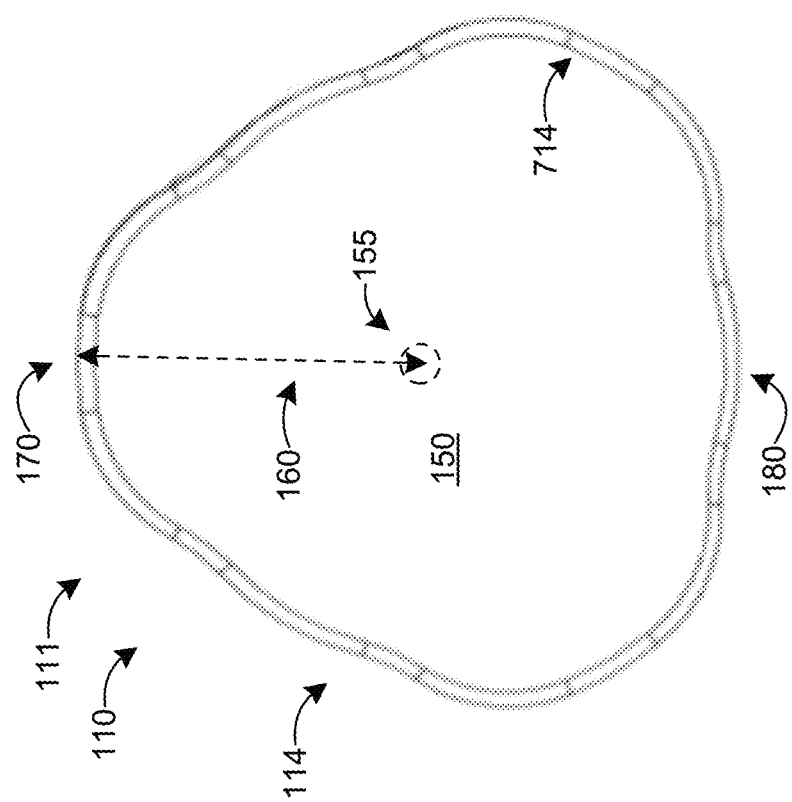
FIG. 7 is a cross-sectional view of the flexible hollow body illustrated in FIG. 5.

FIG. 7 is a cross-sectional view of the flexible hollow body 110 through line 5-5 in FIG. 5. As discussed above and as illustrated in FIG. 7, the flexible hollow body 110 is in a relaxed state in which the cross-sectional shape (e.g., first shape 111) of the flexible hollow body 110 and the channel 150 is irregular. Since the channel 150 is defined by the interior surface 714 of the wall 114 of the flexible hollow body 110, the cross-sectional shape of the wall 114 generally corresponds to the cross-sectional shape of the channel 150. Thus, the channel 150 has the same or substantially the same cross-sectional shape as the flexible hollow body 110.

FIG. 7 also illustrates the largest cross-sectional radius 160 of the flexible hollow body 110. The largest cross-sectional radius 160 can be determined by the length of the longest line that extends from the center or approximate center 155 of the channel 150 to the wall 114 (e.g., to an external surface of the wall 114) of the flexible hollow body 110. In the relaxed state, the largest cross-sectional radius 160 extends to the deformable contact points 170, which are disposed further from the center or approximate center 155 of the channel 150 than the other portions of the wall 114.

Figure 8:
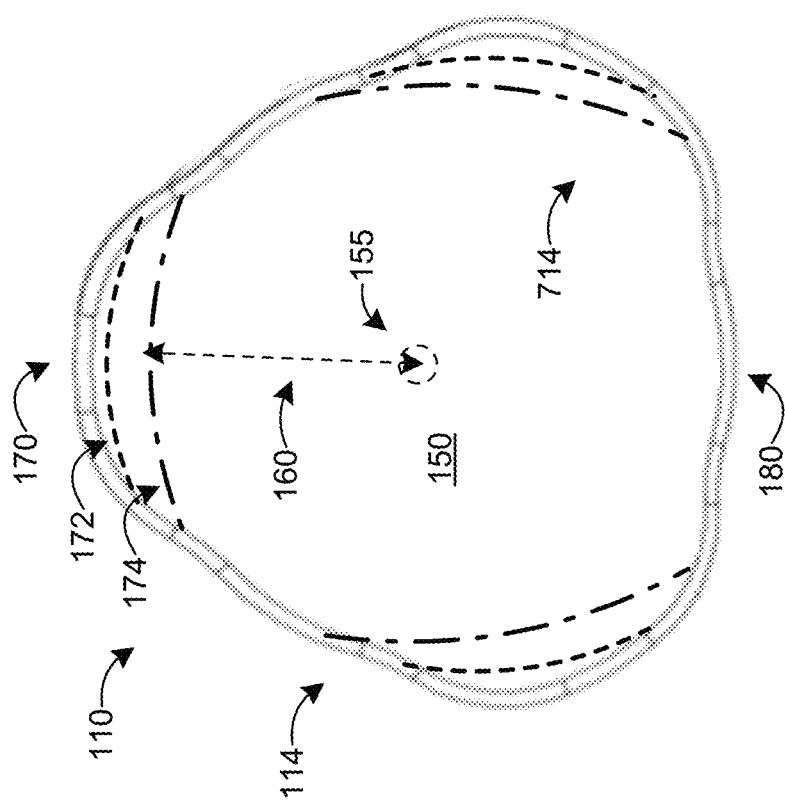
FIG. 8 is a cross-sectional view of the flexible hollow body illustrated in FIG. 6 according to a first embodiment.

FIG. 8 is a cross-sectional view of the flexible hollow body 110 through line 6-6 in FIG. 6. As discussed above and as illustrated in FIG. 8, the flexible hollow body 110 is in a compressed state in which the cross-sectional shape of the flexible hollow body 110 at least partially conforms to the cross-sectional shape of the wall 525 that defines the second channel 520. In the compressed state, the deformable contact points 170 are compressed inwardly such that the largest cross-sectional radius 160 is equal to (or slightly smaller than) the cross-sectional radius of the second channel 520. This compression causes the deformable contact points 170 to exert an outward force against the wall 525, which at least partially secures the flexible hollow body 110 to the wall 525 of the second channel 520. The compression also causes the leaflets 122 of the multi-leaflet valve 120 to close, which increases the cracking pressure, the first and second threshold forces, and the first and second threshold pressure differentials of the multi-leaflet valve 120, as discussed above.

The maximum amount or percentage of deformation of the deformable contact points 170 without damaging the wall 114 is a function of the cross-sectional geometry of the flexible hollow body 110 and the material properties (e.g., hardness) of the flexible hollow body 110. For example, the deformable contact points can deform by a first percentage (e.g., 10%) as indicated by line 172 (e.g., with respect to undeformed contact point 170) or by a second percentage (e.g., 100%) as indicated by line 174. For clarity, the largest cross-sectional radius 160 in FIG. 8 is illustrated only with respect to line 174. Those skilled in the art will appreciate that the amount or percentage of deformation can range from about 1% to about 100% or higher, and can be customizable based on the geometry and/or material properties of the flexible hollow body 110 and the difference between the largest cross-sectional radius 160 in the uncompressed state and the cross-sectional radius 522 of the second channel 520.

Figure 9:
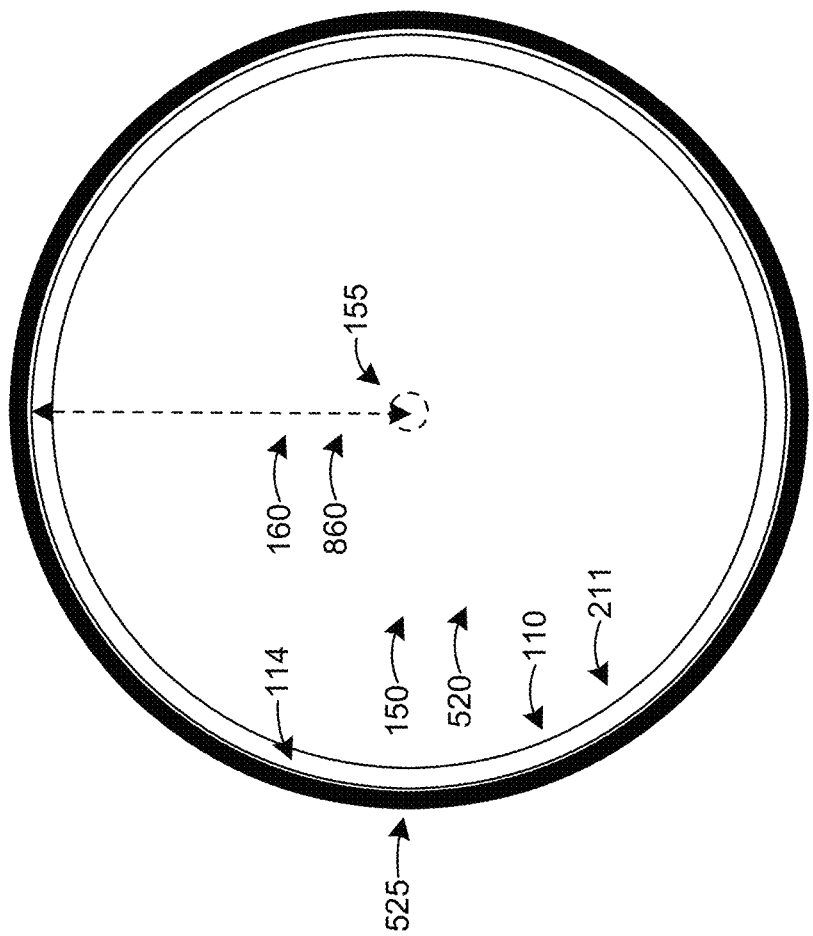
FIG. 9 is a cross-sectional view of the flexible hollow body illustrated in FIG. 6 according to a second embodiment.

In some embodiments, the cross-sectional shape (e.g., second shape 211) of the flexible hollow body 110 in the compressed state is a circle or annulus (e.g., a regular shape), which conforms to the circular or annular cross-sectional shape of the second channel 520 and wall 525, as illustrated in FIG. 9. In the compressed state illustrated in FIG. 9, the largest cross-sectional radius 160 of the flexible hollow body 110 is equal to (or slightly smaller than) the cross-sectional radius 860 of the flexible hollow body 110. Since the wall 114 of the flexible hollow body 110 in the compressed state forms a circle or an annulus, the corresponding cross-sectional shape of the channel 150 is a circle. It is noted that the cross-sectional shapes of the flexible hollow body 110, the wall 525, and the second channel 520 can be other shapes (e.g., ovals or oval rings), as discussed above.

Figure 10:
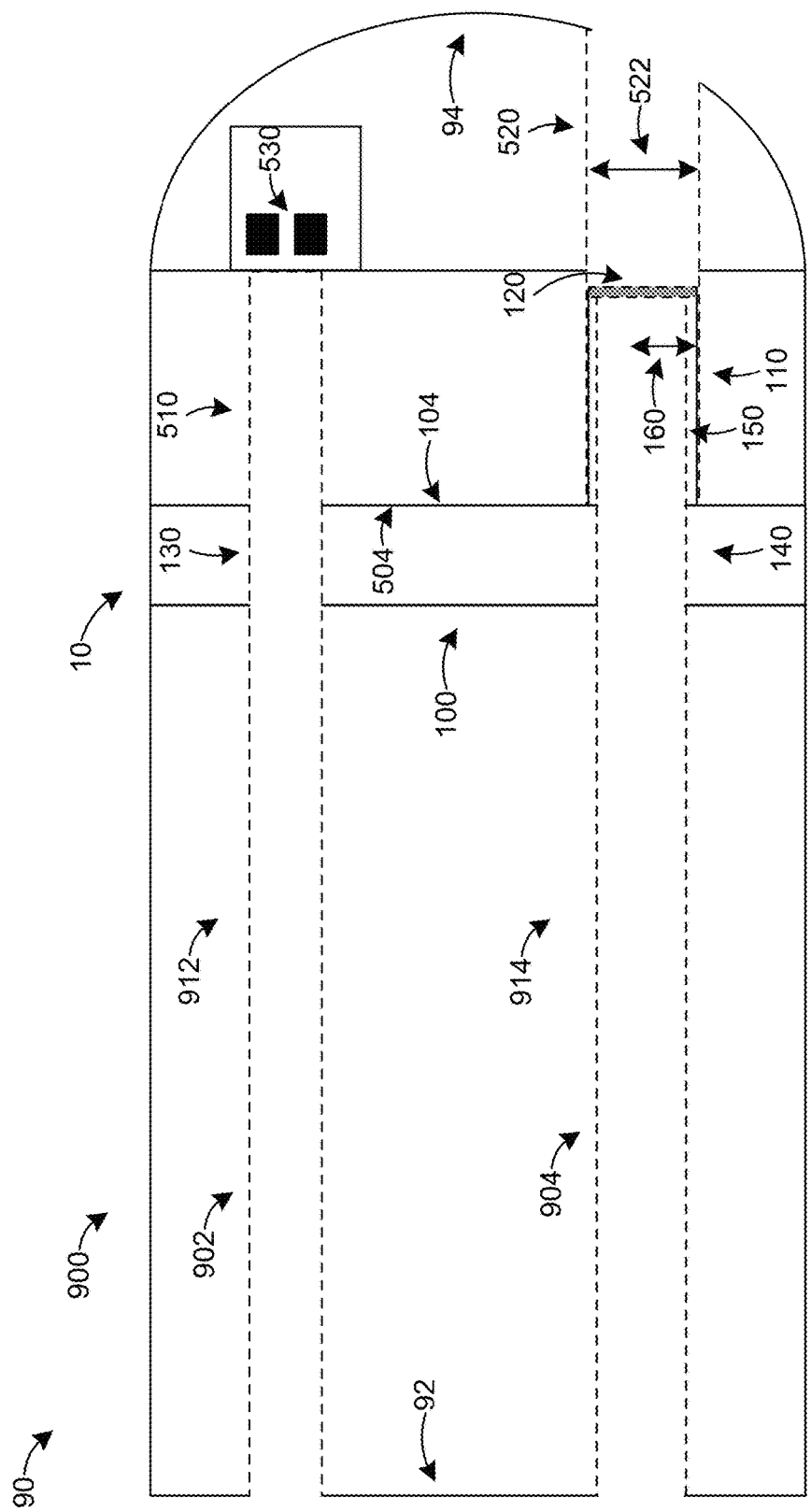
FIG. 10 is a cross-sectional view of an instrument port according to one or more embodiments.

FIG. 10 is a cross-sectional view of an instrument port 90 according to one or more embodiments. The instrument port 90 includes a port body 900, the gasket 10, and the bulb 500. An imaging channel 912 and an instrument channel 904 are defined in the port body 900. The gasket 10 is disposed between the port body 900 and the bulb 500. The second hole 130 in the gasket 10 is aligned with the first channel 902 in the port body 900 and with the first channel 510 in the bulb 500 to form a continuous imaging channel 912. The imaging channel 912 extends from a proximal end 92 of the instrument port 90 to the imaging system 530, which is disposed within the bulb 500. The first hole 140 and channel 150 in the gasket 10 are aligned with the second channel 904 in the port body 900 and with the second channel 520 in the bulb 500 to form a continuous instrument channel 912. The instrument channel 912 extends from the proximal end 92 to a distal end 94 of the instrument port 90.

In operation, the distal end 94 of the instrument port 90 can be inserted into a surgical site or orifice of a subject to guide an instrument (e.g., a surgical instrument) thereto. When the instrument port 90 is inserted into the surgical site or orifice of the subject, it is exposed to bodily fluids such as blood, saliva, and/or urine. Before an instrument is inserted through the instrument channel 914, the multi-leaflet valve 120 is configured (e.g., due to its high cracking pressure or second threshold pressure differential) to prevent such bodily fluids from entering the channel 150 and flowing towards the proximal end 92 of the instrument port 90. The flexible base 100 disposed between the first and second holes 130, 140 further prevents any fluid from passing into the imaging channel 912. However, the multi-leaflet valve 120 is configured to open to allow the instrument to pass through when the instrument applies at least a first minimum force or a first threshold force against the multi-leaflet valve 120 in a distal direction. The first minimum force or first pressure differential required to open the multi-leaflet valve 120 in the distal direction is significantly lower than the second minimum or second threshold force or second pressure differential, respectively, required to open the multi-leaflet valve 120 in the proximal direction such that the multi-leaflet valve 120 effectively operates as a one-way valve in the distal direction. The leaflets 122 apply an inward force against the instrument to close the multi-leaflet valve 120 after the instrument is removed. The multi-leaflet valve 120 is also configured to remain closed when the pressure differential across the multi-leaflet valve 120 is lower than the first or second threshold pressure differential, as discussed above.

In addition, one or more wires can pass through the imaging channel 912 to connect the imaging system 530 with one or more external components, such as a power source and/or a computer. The wires can provide power, data, and/or control signals to/from the imaging system 530. The imaging system 530 can be used to view the instrument as it exits the imaging channel 914 to ensure proper placement of the instrument and/or to guide the procedure.

The present invention should not be considered limited to the particular embodiments described above, but rather should be understood to cover all aspects of the invention as fairly set out in the attached claims. Various modifications, equivalent processes, as well as numerous structures to which the present invention may be applicable, will be apparent to those skilled in the art to which the invention is directed upon review of this disclosure. The claims are intended to cover such modifications and equivalents.

What is claimed is:

1. A gasket for creating a fluid seal in a medical device, the gasket comprising:
   a flexible base;
   a hole defined in the flexible base, the hole sized and arranged to align with a conduit in the medical device;
   a flexible hollow body extending along an axis from the hole, wherein the flexible hollow body is configured to have a relaxed state in which a cross section of the flexible hollow body has a first shape and a compressed state in which the cross section of the flexible hollow body has a second shape, the cross section lying in a plane orthogonal to the axis, wherein an inward force, with respect to the cross section, is applied to a wall of the flexible hollow body to deform at least a portion of the wall inwardly to transition the flexible hollow body from the relaxed state to the compressed state; and
   a multi-leaflet valve disposed in the flexible hollow body, wherein the compressed state causes the multi-leaflet valve to close to increase (a) a first threshold force or a first threshold pressure differential needed to open the multi-leaflet valve in a distal direction and (b) a second threshold force or a second threshold pressure differential needed to open the multi-leaflet valve in a proximal direction.

2. The gasket of claim 1, wherein the multi-leaflet valve is disposed at a distal end of the flexible hollow body and a proximal end of the flexible hollow body is disposed proximal to the hole in the flexible base.

3. The gasket of claim 2, wherein the multi-leaflet valve is configured to open in response to an outward force from a surgical instrument inserted, in the distal direction, through the hole into a channel defined by the flexible hollow body, the outward force greater than or equal to the first threshold force required to open the multi-leaflet valve in the distal direction.

4. The gasket of claim 3, wherein the inward force is a first inward force and the multi-leaflet valve is configured to exert a second inward force against the surgical instrument to close the multi-leaflet valve when the surgical instrument is removed therefrom.

5. The gasket of claim 1, wherein the first threshold pressure differential required to open the multi-leaflet valve in the distal direction is lower than the second threshold pressure differential required to open the multi-leaflet valve in the proximal direction.

6. The gasket of claim 1, wherein an exposed surface of the multi-leaflet valve curves inwardly towards the flexible hollow body, the exposed surface facing away from the flexible hollow body.

7. The gasket of claim 6, wherein the exposed surface is concave.

8. The gasket of claim 1, wherein the flexible hollow body is in the compressed state when the flexible hollow body is inserted into the conduit in the medical device.

9. The gasket of claim 8, wherein a conduit radius of the conduit in the medical device is smaller than a largest cross-sectional radius of the flexible hollow body in the relaxed state.

10. The gasket of claim 9, wherein the flexible hollow body exerts an outward force towards a wall of the conduit in the medical device to at least partially secure the flexible hollow body to the wall of the conduit.

11. The gasket of claim 1, wherein the gasket comprises silicone.

12. The gasket of claim 1, wherein the first shape is irregular and the second shape is annular.

13. The gasket of claim 1, wherein a second hole is defined in the flexible base, the second hole sized and arranged to align with a second conduit in the medical device.

14. An instrument port for introducing an instrument into a surgical site, the instrument port comprising:
 a port body having a port body channel that extends from a proximal end to a distal end of the port body;
 a bulb comprising a bulb channel; and
 a gasket disposed between the port body and the bulb, the gasket comprising:
  a flexible base;
  a hole defined in the flexible base, the hole sized and arranged to align with the port body channel and the bulb channel to thereby form a continuous instrument channel;
  a flexible hollow body extending along an axis from the hole, wherein the flexible hollow body is configured to have a relaxed state in which a cross section of the flexible hollow body has a first shape and a compressed state in which the cross section of the flexible hollow body has a second shape, the cross section lying in a plane orthogonal to the axis, the flexible hollow body transitioning to the compressed state when the flexible hollow body is inserted into the bulb channel, wherein an inward force, with respect to the cross section, is applied to a wall of the flexible hollow body to deform at least a portion of the wall inwardly to transition the flexible hollow body from the relaxed state to the compressed state; and
  a multi-leaflet valve disposed in the flexible hollow body, wherein:
   the compressed state causes the multi-leaflet valve to close to increase (a) a first threshold force or a first threshold pressure differential needed to open the multi-leaflet valve in a distal direction and (b) a second threshold force or a second threshold pressure differential needed to open the multi-leaflet valve in a proximal direction.

15. The instrument port of claim 14, wherein the flexible hollow body exerts an outward force towards a wall of the bulb channel to at least partially secure the flexible hollow body to the wall of the bulb channel.

16. The instrument port of claim 14, wherein the multi-leaflet valve is disposed at a distal end of the flexible hollow body and a proximal end of the flexible hollow body is disposed proximal to the hole in the flexible base.

17. The instrument port of claim 14, wherein the multi-leaflet valve is configured to open in response to an outward force from a surgical instrument inserted through the instrument channel in the distal direction, the outward force greater than or equal to the first threshold force required to open the multi-leaflet valve in the distal direction.

18. The instrument port of claim 17, wherein the inward force is a first inward force and the multi-leaflet valve is configured to exert a second inward force against the surgical instrument to close the multi-leaflet valve when the surgical instrument is removed therefrom.

19. The instrument port of claim 14, wherein the first threshold pressure differential required to open the multi-leaflet valve in the distal direction is lower than the second threshold pressure differential required to open the multi-leaflet valve in the proximal direction.

20. The instrument port of claim 14, wherein an exposed surface of the multi-leaflet valve curves inwardly towards the flexible hollow body, the exposed surface facing away from the flexible hollow body.

21. The instrument port of claim 20, wherein the exposed surface is concave.

22. The instrument port of claim 14, wherein:
 a bulb channel radius of the bulb channel is smaller than a largest cross-sectional radius of the flexible hollow body when the flexible hollow body is in the relaxed state,
 the largest cross-sectional radius of the flexible hollow body is less than or equal to the bulb channel radius when the flexible hollow body is the compressed state, and
 the inward force is applied by a wall of the bulb channel.

23. The instrument port of claim 14, wherein the gasket comprises silicone.

24. The instrument port of claim 14, wherein the first shape is irregular and the second shape is annular.

25. The instrument port of claim 14, wherein a second hole is defined in the flexible base, the second hole sized and arranged to align with a second port body channel and a second bulb channel to thereby form a continuous imaging channel.

26. The instrument port of claim 25, wherein the second bulb channel extends to an imaging system disposed within the bulb.

27. The instrument port of claim 14, wherein the inward force is applied by a wall of the bulb channel flexible hollow body.

* * * * *

UNITED STATES PATENT AND TRADEMARK OFFICE
CERTIFICATE OF CORRECTION

PATENT NO. : 11,213,316 B2
APPLICATION NO. : 15/917126
DATED : January 4, 2022
INVENTOR(S) : Anthony Maiorano et al.

It is certified that error appears in the above-identified patent and that said Letters Patent is hereby corrected as shown below:

In the Specification

Column 1, Lines 7, after "with" delete -- U.S. --;

Column 1, Lines 8-10, delete "5R42HL132655, awarded by the Heart, Lung, and Blood Institute (NHLBI) of the National Institutes of Health (NIH)" and insert -- HL132653, awarded by the National Institutes of Health --;

Column 1, Line 10, delete "U.S. government" and insert -- Government --.

Signed and Sealed this
Twenty-fourth Day of December, 2024

Derrick Brent
*Acting Director of the United States Patent and Trademark Office*